(12) United States Patent
Yoon et al.

(10) Patent No.: US 6,433,190 B1
(45) Date of Patent: Aug. 13, 2002

(54) 3,6-DI(3',5'-BIS(FLUOROALKYL) PHENYL) PYROMELLITIC DIANHYDRIDE AND METHOD FOR THE PREPARATION THEREOF

(75) Inventors: Tae-Ho Yoon; Bum-Young Myung, both of Kwangju (KR)

(73) Assignee: Kwangju Institute of Science and Technology, Kwangju (KR)

( * ) Notice: Subject to any disclaimer, the term of this patent is extended or adjusted under 35 U.S.C. 154(b) by 81 days.

(21) Appl. No.: 09/828,974

(22) Filed: Apr. 10, 2001

(30) Foreign Application Priority Data

Jan. 26, 2001 (KR) .............................................. 01-3813

(51) Int. Cl.⁷ ............................................ C07D 493/02
(52) U.S. Cl. ..................................................... 549/239
(58) Field of Search .................................. 549/236, 239

(56) References Cited

U.S. PATENT DOCUMENTS 4,360,657 A * 11/1982 Nimry et al. ................ 528/188

OTHER PUBLICATIONS

Res. Res. Devel. in Polymer Science, 2 (1998) 509–538.*
J. photopolym. Sci. Technol. (1995). 8 (2), 325–328 CAS Abstract.*

"Abstracts" titled "Synthesis and Characterization of Novel Polyimides Containing Bis (trifluoromethyl) phenyl Pendent Moiety" dated Oct. 25, 2000 by The Polymer Society of Korea.

Akira Sekiya and Nobuo Ishikawa, Palladium Metal–Catalyzed Cross–Coupling of Aryl Iodides with Arylmagnesium Bromides. Synthesis of Fluoroeiphenyls, Journal of Organometallic Chemistry, 125 (1977)pp. 281–290.

N. Miyaura, T. Yanagi, and A. Suzuki, the Palladium–Catalyzed Cross–Coupling Reaction of Phenyboronic Acid with Haloarenes in the Presence of Bases, Synthetic Communications. 11(7), pp. 513–519, (1981).

* cited by examiner

Primary Examiner—Joseph K. McKane
Assistant Examiner—Kamal Saeed
(74) Attorney, Agent, or Firm—Lowe Hauptman Gilman & Berner, LLP

(57) ABSTRACT

The present invention relates to fluorine-containing 3,6-di (3',5'-bis(trifluoromethyl)benzene)pyromellitic dianhydride as a monomer which can be used in preparing polyimides with high glass transition temperature, low dielectric constant and excellent processability, and preparing method thereof.

8 Claims, 4 Drawing Sheets

3,6-DI(3',5'-BIS(FLUOROALKYL) PHENYL) PYROMELLITIC DIANHYDRIDE AND METHOD FOR THE PREPARATION THEREOF

BACKGROUND OF THE INVENTION

FIELD OF THE INVENTION

The present invention relates to fluorine-containing 3,6-di(3',5'-bis(trifluoromethyl)benzene)pyromellitic dianhydride as a monomer which can be used in preparing polyimides with high glass transition temperature, low dielectric constant and excellent processability, and preparing method thereof.

Polyimide is widely used as film, resin, molded part, adhesive and insulator for electronic, automotive and aerospace applications due to its superior heat resistance, mechanical property and electric property.

Especially, its use is increasing for insulating layer of semiconductor chips in electronic industry due to its superior dielectric property and thermal/chemical stability. However, it still has a number of drawbacks to be solved for high performance electronic devices which are getting smaller and lighter. Therefore, the polyimide with low dielectric constant, high glass transition temperature and superior processability is needed to be prepared for integrated multi-layer chip applications.

According to the recent research works, polyimide synthesized from monomers containing fluorine, which has small van der Waals radius, large electro-negativity and high reactivity to other element, shows superior solubility, low water absorption and low dielectric constant. However, the introduction of fluorine substituent into polyimide also lowers the glass transition temperature. Accordingly, the synthesis of fluorine-containing monomer with rigid structure is required to obtain polyimide with low dielectric constant and high glass transition temperature.

SUMMARY OF THE INVENTION 3,6-di(3',5'-bis(trifluoromethyl)benzene)pyromelliticdianhydride was prepared as a novel monomer by combining 3,5-bis(trifluoromethyl)benzene, which is a flucorine-containing benzene substituent, and pyromellitic dianhydride derivative having rigid backbone structure. Polyimide prepared from this monomer has high glass transition temperature, low dielectric constant, low water absorption and superior solubility. Therefore, its application can be expanded to electronic devices.

DETAILED DESCRIPTION OF THE INVENTION

Figure 1:
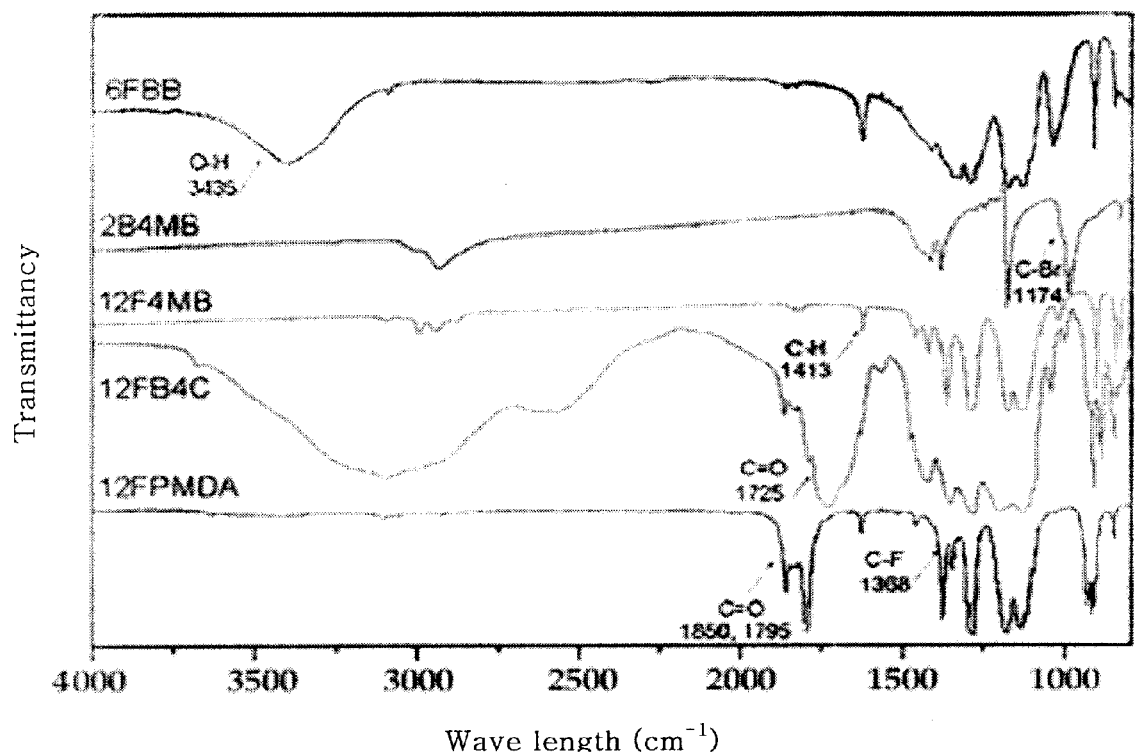
FIG. 1 is FT-IR spectra for the compounds synthesized from Examples 1-5.

The present invention describes 3,6-di(3',5'-bis(trifluoromethyl)benzene)pyromelliticdianhydride expressed by the following formula (1), and preparing method thereof,

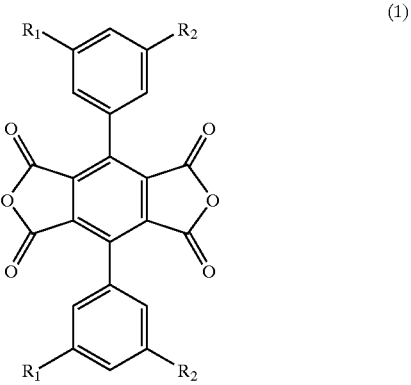

wherein $R_1$ and $R_2$ may be identical or different and represent fluorine-substituted $C_1$–$C_9$ alkyl group.

The preparation of the novel monomer expressed by formula (1) is represented by the following Scheme 1,

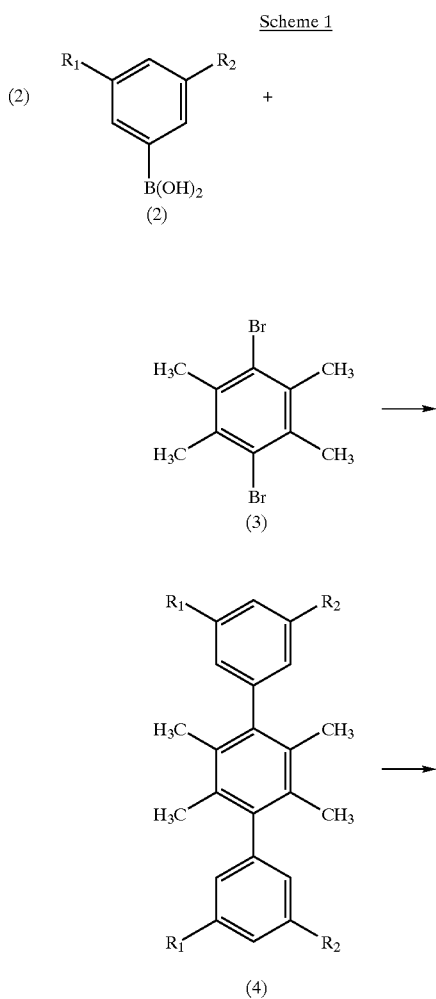

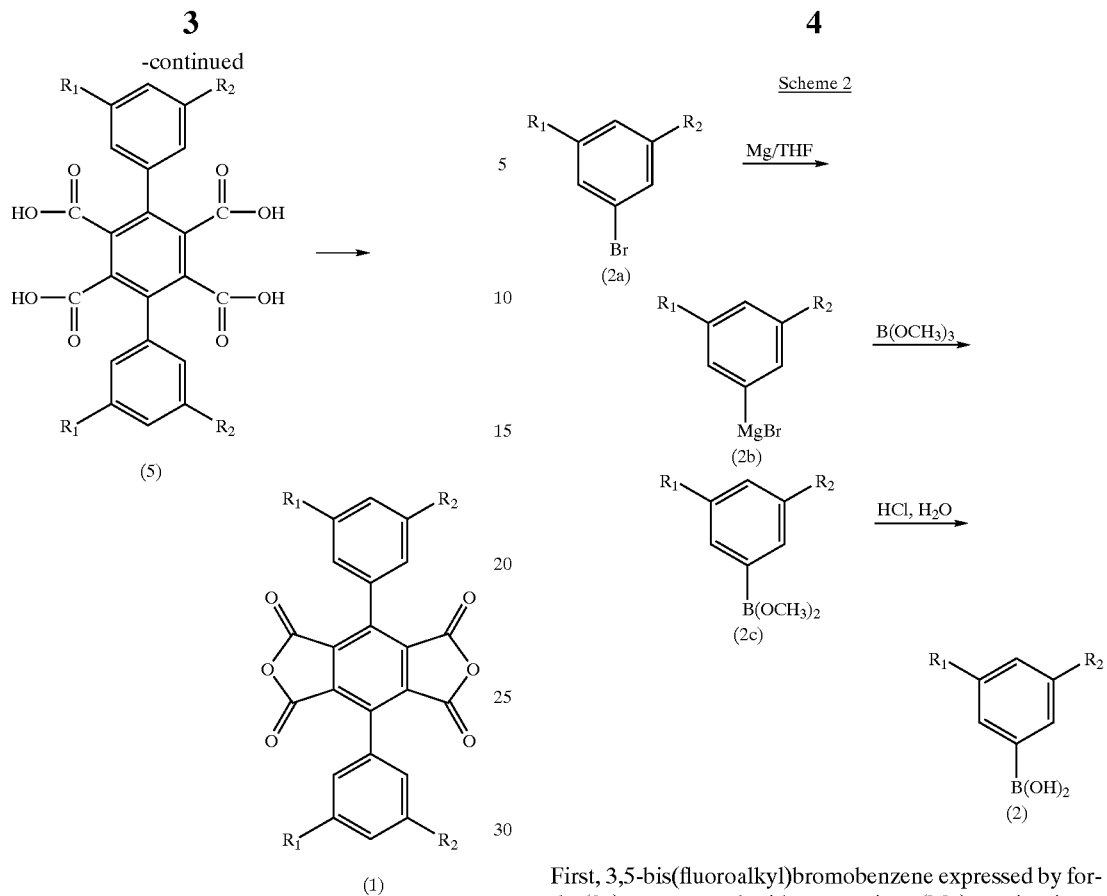

wherein $R_1$ and $R_2$ may be identical or different, and represent fluorine-substituted $C_1$–$C_9$ alkyl group.

The compound expressed by formula (4) was obtained by refluxing the compounds expressed by formula (2) and formula (3) in the presence of tetrakis(triphenylphosphine) palladium ($[(C_6H_5)_3P]_4Pd$) (catalyst), alkaline metal carbonate or alkaline metal bicarbonate aqueous solution, ethanol and organic solvent such as toluene. The reflux temperature was the boiling point of the solvent used, preferably, 85–95° C. The molar ratio of the compounds expressed by formula (2) and formula (3) was 3~2:1, and the reaction catalyst was in the range of 0.01–0.1 mol % of the compound (3).

The carboxyl groups were introduced to the compound expressed by formula (4) via oxidizing methyl groups, which was carried out by refluxing the compound expressed by formula (4) and excessive potassium permanganate ($KMnO_4$) in pyridine and distilled water for 5 hours at 90–98° C. The product was filtered and dried, and then refluxed again in sodium hydroxide (NaOH) aqueous solution with excessive potassium permanganate at 90–98° C. for 5 hours, resulting in alkaline aqueous solution. After filtering that solution, hydrochloric acid (HCl) was added to get precipitate which was then washed with distilled water and dried to obtain the compound expressed by formula (5).

The compound expressed by formula (5) was further dried at 200–300° C. in a vacuum oven (20–40 in Hg) to afford the monomer expressed by formula (1).

The compounds expressed by formulas (2) and (3), which were used for the preparation of the compound expressed by formula (1), were prepared as follows.

The compound expressed by formula (2) can be prepared by the following Scheme 2.

First, 3,5-bis(fluoroalkyl)bromobenzene expressed by formula (2a) was reacted with magnesium (Mg) turning in an organic solvent like tetrahydrofuran at 0–5° C. for 12 hours, and then, the reaction mixture was allowed to reach further room temperature to afford the compound expressed by formula (2b). The compound expressed by formula (2c) was obtained via Grignard reaction; reacting the compound expressed by formula (2b) with trimethylborate ($B(OCH_3)_3$) at $-75$~$-65°$ C. and then at room temperature for 12 hours, and the molar ratio was 1:1. By hydrolyzing the compound expressed by formula (2c) in hydrochloric acid aqueous solution at 0–5° C., the compound expressed by formula (2) was obtained.

The compound expressed by formula (3) can be prepared by the following Scheme 3.

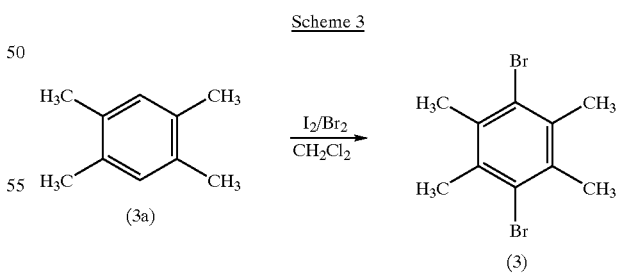

After dissolving 1,2,4,5-tetramethylbenzene expressed by formula (3a) and iodine ($I_2$) into an organic solvent such as dichloromethane ($CH_2Cl_2$), bromine ($Br_2$) was slowly added under the shielding of light. Then the reaction mixture was allowed to react at 40–50° C. for 1 hour to give the compound expressed by formula (3). In this reaction, the molar ratio of the compound expressed by formula (3a), iodine ($I_2$) and bromine ($Br_2$) was approximately 1:0.01–0.1:2.0–3.0.

Hereunder is given the more detailed description of the present invention using examples. However, it should not be construed as limiting the scope of the present invention.

EXAMPLE 1

Preparation of 3,5-bis(tri(fluoromethyl) benzeneboronic acid (formula (2); 6FBB)

After drying a 500 mL 3-neck round-bottom flask, equipped with magnetic stirrer, dropping funnel, condenser and nitrogen inlet, 9.30 g of magnesium turning (Aldrich) and 220 mL of tetrahydrofuran were added, and then the reaction mixture was cooled to 0–5° C. using an iced bath. 44. 0 mL of 3,5-bis(trifluoromethyl)bromobenzene was added slowly over a period of 1 hr using a dropping funnel, while maintaining the temperature of 0–5° C. Then, the reaction solution was allowed to reach room temperature and further reacted for 16 hr at room temperature. After having a dark brown viscous solution, 28. 97 mL of trimethylborate was added under nitrogen flow, while maintaining −75~−65° C. using dry ice and acetone.

The reaction mixture was allowed to reach the room temperature, and the reacted further for 24 hours to give a brown viscous solution. While maintaining the temperature of this viscous solution at 0–5° C., the mixture of 144. 5 mL of distilled water and 63. 3 mL of hydrochloric acid (37 wt %) was added to the solution mixture, and it was further reacted for 12 hr. The resultant formed two layer; dark-red organic layer and aqueous layer, and the organic layer was separated by using a separation funnel. In order to remove salts remaining in the organic layer, distilled water was added into the organic layer, followed by shaking vigorously and then decanting of aqueous layer. Then, the organic part was evaporated to afford white crystal which was further purified by recrystallization in distilled water and washing with petroleum ether. The monomer was dried at room temperature for 24 hr and 19.44 g of the target compound was obtained (yield: 65%).

The monomer was characterized by FT-IR, $^1$H-NMR, $^{19}$F-NMR and melting point measurement. The FT-IR analysis provided C—F bond peaks at 1368, 1284 and 1186 cm$^{-1}$ aromatic C=C stretching peaks at 1612 and 1418 cm$^{-1}$; and a broad O—H peak at 3400 cm$^{-1}$ as in FIG. 1. The $^1$H-NMR analysis (CDCl$_3$) showed proton peaks of benzene at 8.215 and 7.974 ppm, and that from O—H at 4.795 ppm, while $^{19}$F-NMR (with CDCl$_3$) showed a single peak at −41.194 ppm. The melting point was in the range of 218.6–220.0° C. FT-IR and NMR analysis clearly demonstrated successful preparation of the target product.

EXAMPLE 2

3,6-Dibromo-1,2,4,5-tetramethylbenzene (formula (3); 2B4MB)

After drying a 150 mL 4-neck round-bottom flask, equipped with magnetic stirrer, dropping funnel, condenser and nitrogen inlet, 8.0 g of 1,2,4,5-tetramethylbenzene, 0.124 g of iodine ($I_2$) and 23.84 mL of dichloromethane (CH$_2$Cl$_2$) were charged into the flask and completely dissolved. Then, 22.86 mL of bromine ($Br_2$) was added to this solution mixture via dropping funnel over a period of 2 hr, followed by further reaction at 40–50° C. for 1 hr. The entire reactor was covered with aluminum foil to prevent the side reaction of bromine ($Br_2$) caused by light. The final reactant was mixed with a small amount of 5N sodium hydroxide (NaOH) aqueous solution in order to remove the unreacted bromine, forming organic layer and aqueous solution layer. The organic layer was isolated and a small amount of magnesium sulfate (MgSO$_4$) was added in order to remove the remaining water in the organic layer. Then, the organic part was filtered, followed evaporation to afford solid residue. The monomer was recrystallized in dichloromethane (CH$_2$Cl$_2$), resulting in white crystal of 3,6-dibromo-1,2,4,5-tetramethylbenzene (16. 53 g, yield: 95%), the target compound.

Figure 2:
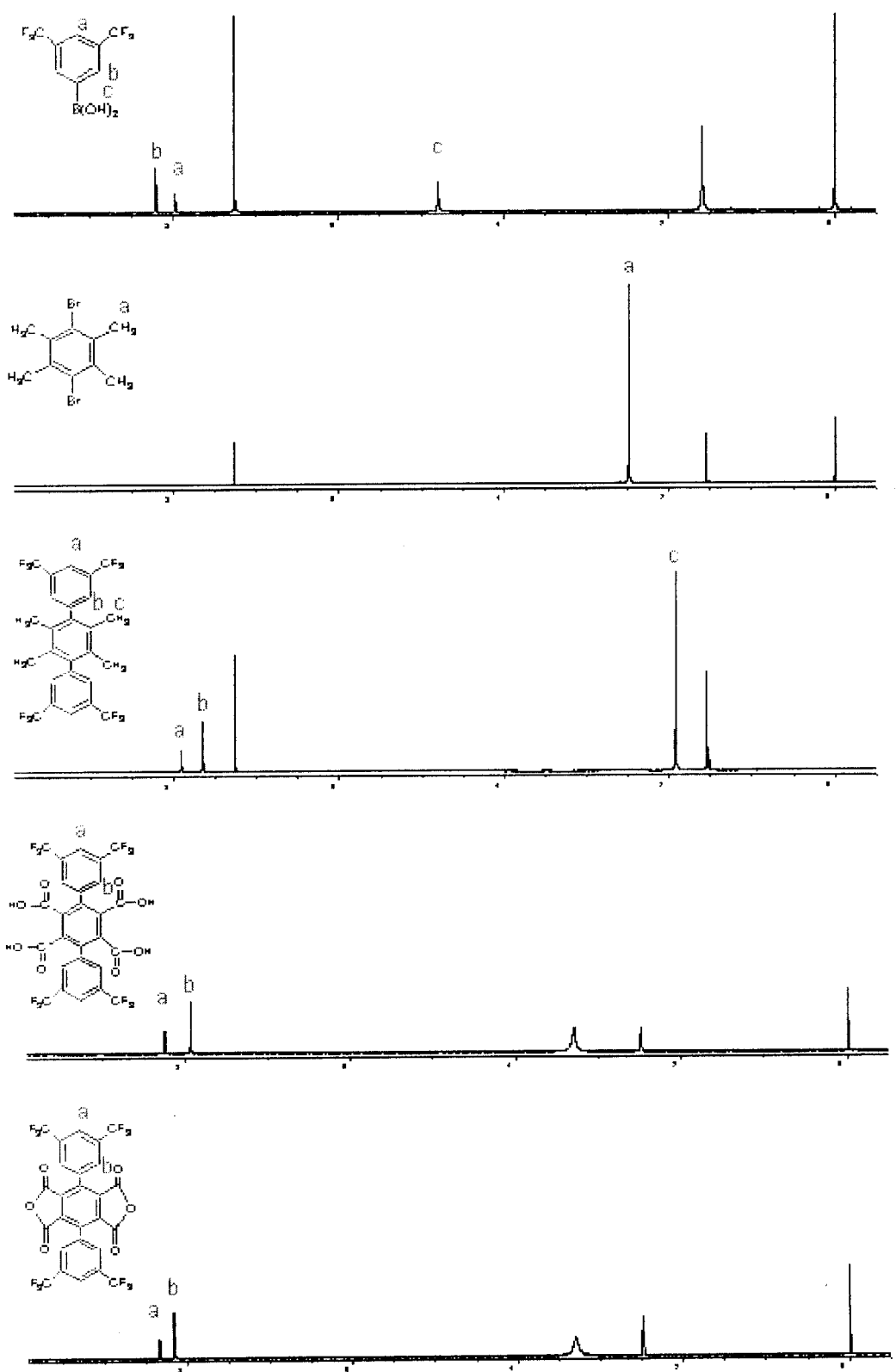
FIG. 2 is $^1$H-NMR spectra for the compounds synthesized from Examples 1-5.
Figure 3:
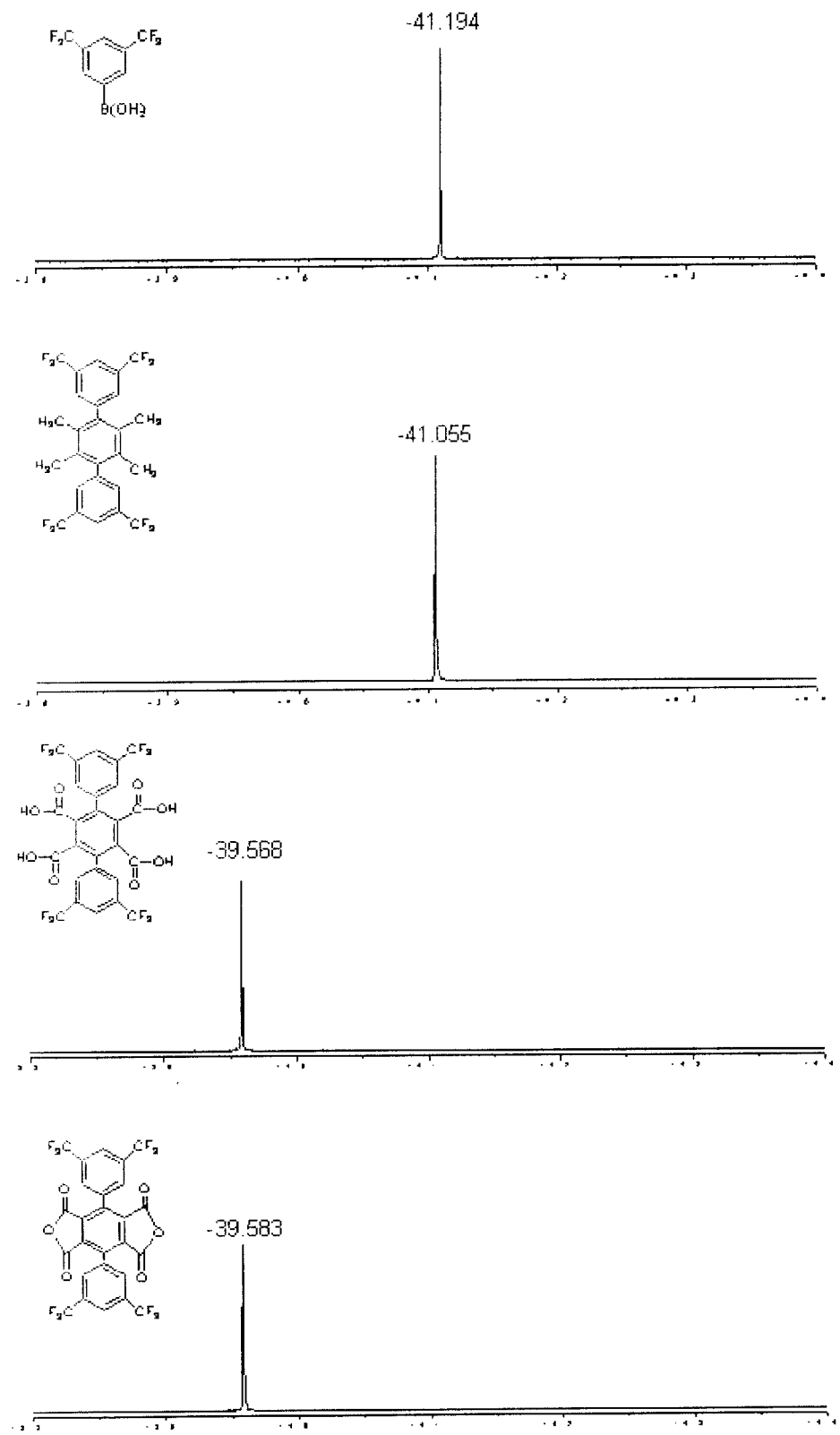
FIG. 3 is $^{19}$F-NMR spectra for the compounds synthesized from Examples 1-5.

The melting point was in the range of 198.5–199. 5° C. The FT-IR analysis showed a C—Br bond peak at 1174 cm$^{-1}$; an aromatic C=C stretching peak at 1413 cm$^{-1}$; and a broad C—H peak from CH$_3$ at 2934 cm$^{-1}$ as shown in FIG. 1. The $^1$H-NMR analysis (with CDCl$_3$) showed proton peak from CH$_3$ at 2.488 ppm as shown in FIG. 2, demonstrating successful preparation of 3,6-dibromo-1,2,4,5-tetramethylbenzene.

EXAMPLE 3

3,6-Di(3',5'-bis(trifluoromethyl)benzene) tetramethylbenzene (formula (4); 12F4MB)

First, 6.23 g of 3,6-dibromo-1,2,4,5-tetramethylbenzene (formula (3)) and 270 mL of toluene were charged into a 1000 mL 3-neck round-bottom flask, equipped with magnetic stirrer, dropping funnel, condenser and nitrogen inlet, and allowed to dissolve completely. Then, 135 mL of 2N sodium carbonate (Na$_2$CO$_3$) and 0.6422 g of tetrakis (triphenylphosphine)palladium ([(C$_6$H$_5$)$_3$P]$_4$Pd)were added to the mixture. After confirming a homogenous mixing, 43 g of 3,5-bis(trifluoromethyl)benzeneboronic acid (formula (2)) in 67.53 mL of ethanol was added, and then it was heated to the boiling point (85–95° C.), flowed by reacting for 7 days. When the color of the reaction mixture changed from orange to dark-red, the mixture was filtered and then transferred to separation funnel. After allowing to form organic layer and aqueous layer, the organic layer was isolated and dried by adding a small amount of magnesium sulfate (MgSO$_4$), followed by stirring for 1 hr. After filtering, the solution was evaporated, resulting in solid residue which was recrystallized in 500 mL of ethyl acetate. The final product, 3,6-di(3',5'-bis(trifluoromethyl)benzene)-1,2,4,5-tetramethylbenzene was obtained (22.96 g, yield: 70%).

3,6-di(3',5'-bis(trifluoromethyl)benzene)-1,2,4,5-tetramethylbenzene was characterized by measuring melting point and analysis by FT-IR, $^1$H-NMR and $^{19}$F-NMR. The melting point was in the range of 246. 7–246. 9° C. The FT-IR analysis showed C—F bond peaks at 1368, 1284 and 1186 cm$^{-1}$; aromatic C=C stretching peaks at 1612 and 1418 cm$^{-1}$; and a broad alkyl C—H peak at around 2934 cm$^{-1}$ as shown in FIG. 1. The $^1$H-NMR analysis (with CDCl$_3$) showed benzene proton peaks at 7.911 ppm and 7.652 ppm; and that from CH$_3$ at 1.9229 ppm. $^{19}$F-NMR analysis (CDCl$_3$) showed single peak from CF$_3$ at −41. 055 ppm.

EXAMPLE 4

3,6-Di(3',5'-bis(trifluoromethyl)benzene)-1,2,4,5-benzenetetracarboxylic acid (Formula (5); 12FB4C)

First, 2.96 g of 3,6-di(3',5'-bis(trifluoromethyl)beizene)-1,2,4,5-tetramethylbenzene (formula 4) was dissolved in 479.5 mL of pyridine in a 1000 mL 3-neck round-bottom flask, equipped with magnetic stirrer, dropping funnel and condenser, and then, 63.93 mL of distilled water was added. This reaction mixture was then heated to the boiling point (90–98° C.) and then 30. 73 g of potassium permanganate was added slowly over a period of 4 hr using, a dropping funnel. The reaction mixture was allowed to react until the color of the solution changed from purple to black, and the further reacted for 1 more hour. Finally, potassium permanganate in the aqueous solution was removed by filtering and the remaining solution was distilled off to afford solid residue. The solid residue and 25.57 g of sodium hydroxide were dissolved in 400 mL of distilled water in a 1000 mL 3-neck round-bottom flask, equipped with magnetic stirrer, dropping funnel and condenser, and heated to the boiling point (90–98° C.) of the reaction mixture. While keeping boiling, 30.73 g of potassium permanganate was added into this solution over a period of 4 hr using a dropping funnel, followed by allowing 1 hour. After lowering the temperature of reaction mixture to approximately 80° C., 31 mL of ethanol was added to form salts with unreacted potassium permanganate, immediate followed by filtering off the salts. The aqueous solution was acidified with hydrochloric acid to afford white crystal. By filtering, washing with distilled water, 3,6-di(3',5'-bis(trifluoromethyl)benzene)-1,2,4,5-tetramethylbenzene (13.18 g, yield: 50%) was obtained.

The structure of 3,6-di(3',5'-bis(trifluoromethyl)benzene)-1,2,4,5-tetramethylbenzene was confirmed by measuring melting point, and by analyzing with FT-IR, $^1$H-NMR and $^{19}$F-NMR. The melting point was in the range of 339.0–340.2° C. The FT-IR analysis showed C—F bonds at 1368, 1284 and 1186 cm$^{-1}$; aromatic C=C stretching peaks at 1612 and 1418 cm$^{-1}$; a carboxylic C=O bond at 1728 cm-$^{-1}$; and a broad O—H peak at around 3400 cm$^{-1}$ as shown in FIG. 1. The $^1$H-NMR analysis (DMSO-d$_6$) revealed that the proton peaks of benzene were shown at 8.2646 ppm and 7.92516 ppm, while sharp single peak was obtained at −39.579 ppm from the $^{19}$F-NMR analysis (DMSO-d$_6$).

EXAMPLE 5

3,6-Di(3',5'-bis(trifluoromethyl)benzene)pyromellitic dianydride (Formula (1); 12FPMDA)

The target compound, 13.18 g of 3,6-di(3',5'-bis(trifluoromethyl)benzene) pyromellitic dianydride) was obtained by baking 3,6-di(3',5'-bis(trifluoromethyl)benzene)-1,2,4,5-benzenetetracarboxylic acid (12FB4C) (Formula 5) at 250° C. for 12 hr under reduced pressure (30 in Hg), followed by subliming at 290° C. under reduced pressure (30 in Hg) (10 g, yield: 80%).

Figure 4:
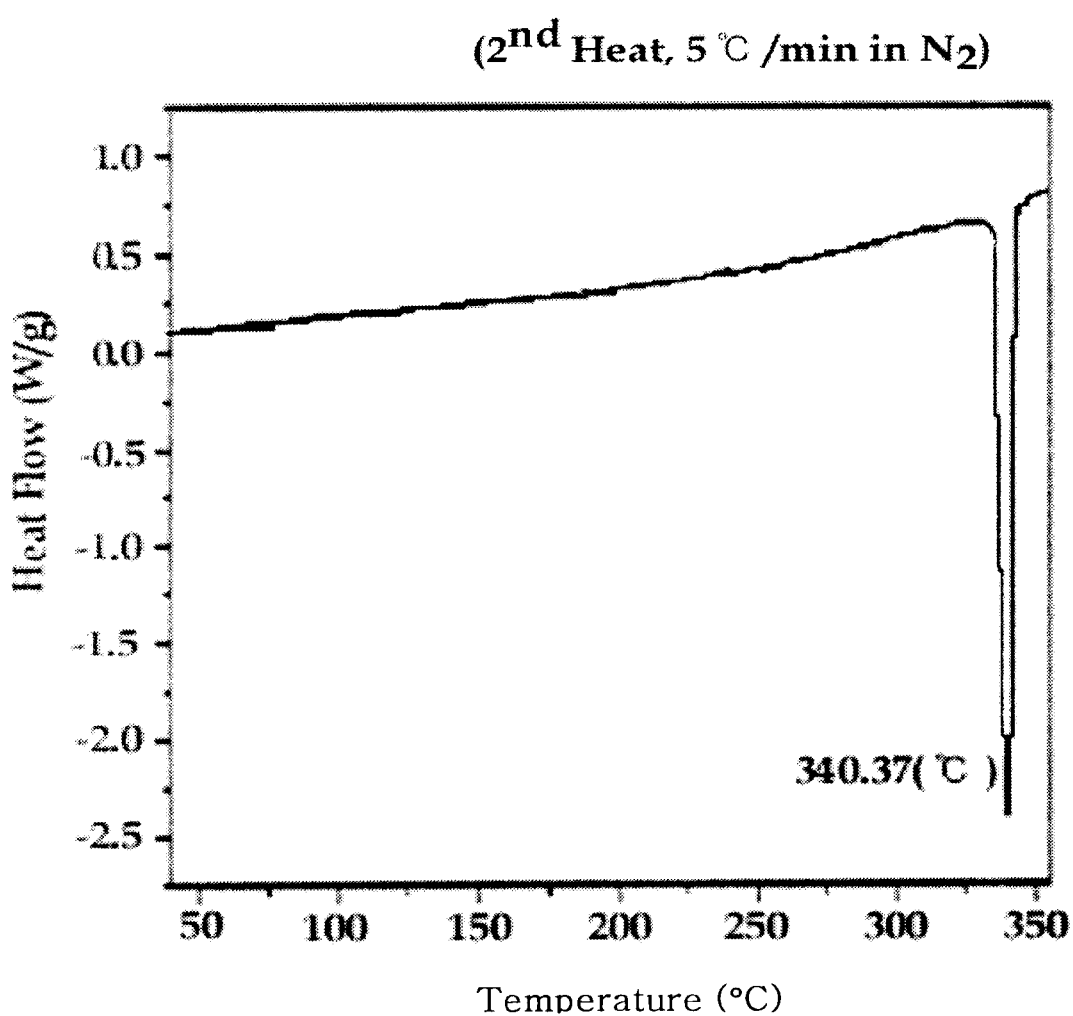
FIG. 4 is DSC thermogram (melting) of Example 5 (12PMDA).

The melting point of the monomer was 340. 37° C. by DSC as shown in FIG. 4. The FT-IR analysis showed C—F bonds at 1368, 1284 and 1186 cm$^{-1}$; aromatic C=C stretching peaks at 1612 and 1418 cm$^{-1}$; a C=O bond of anhydride groups at 1850 cm$^{-1}$ as shown in FIG. 1. The $^1$H-NMR analysis (DMSO-d$_6$) showed proton peaks of benzene at 8.4160 ppm and 8.1786 ppm as shown in FIG. 2. The single peak was observed from $^{19}$F-NMR analysis (with DMSO-d$_6$). The data from FT-IR and NMR confirm the successful preparation of 3,6-di(3',5'-bis(trifluoromethyl)benzene) pyromellitic dianydride.

A novel monomer, 3,6-di(bis(trifluoromethyl)benzene) pyromellitic dianhydride (12FPMDA) expressed by formula (1), has small van der Waals radius and rigid structure. Therefore, the polyimide synthesized with this monomer will be useful for the electronic applications since it has high glass transition temperature, low dielectric constant and good processability.

What is claimed is:

1. 3,6-Di(3',5'-bis(fluoroalkyl phenyl) pyromellitic dianhydride having the following formula (1),

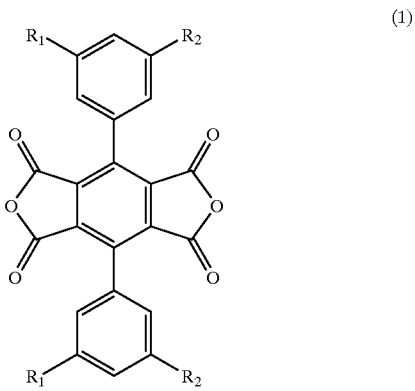

(1)

wherein $R_1$ and $R_2$ are identical or different and each represents a fluorine-substituted $C_1$-$C_9$ alkyl group.

2. A method of preparing the compound expressed by the following Formula (1),

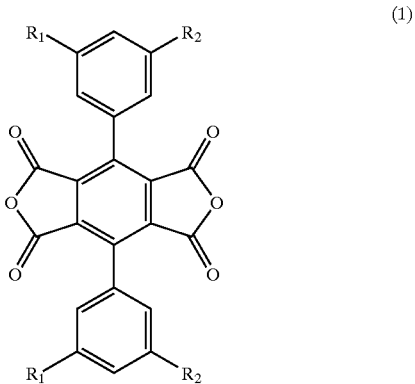

(1)

which comprises:

refluxing a compound of having the following Formula (2) with a compound of the following Formula (3) in the presence of tetrakis(triphenyl phosphine)palladium ($((C_6H_5)_3P)_4Pd$) catalyst under conditions sufficient to produce a compound of the following Formula (4);

refluxing the produced compound of the following Formula (4) with an excess amount of potassium permanganate ($KMnO_4$) under conditions sufficient to produce a compound of the following Formula (5); and drying the obtained compound of Formula (5) at about 200–300° C. and 20–40 inches of Hg reduced pressure to obtain a compound of the following Formula (1):

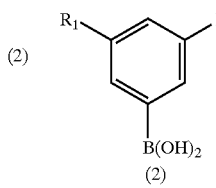

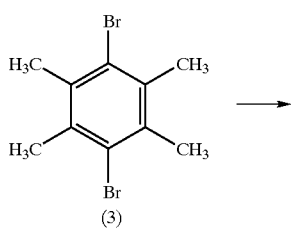

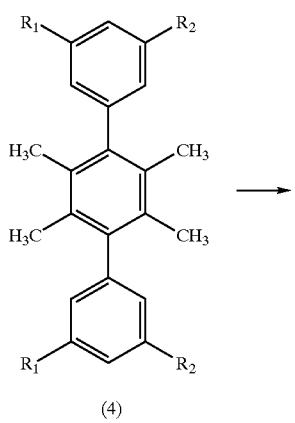

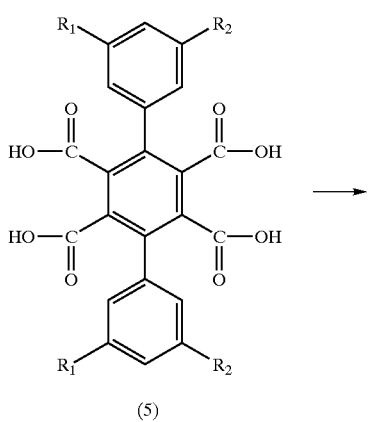

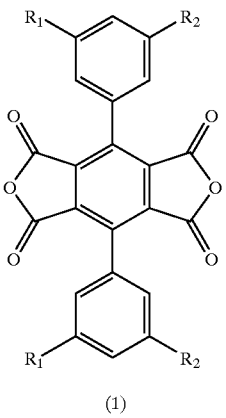

wherein $R_1$ and $R_2$ are identical or different and represent fluorine-substituted $C_1$-$C_9$ alkyl groups.

3. A method according to claim 2, additionally comprising reacting 3,5-bis(fluoroalkyl)bromobenzene, having the following Formula (2a),

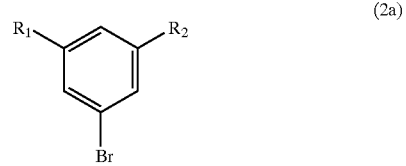

with trimethylborate ($B(OCH_3)_3$) in tetrahydrofuran (THF) in the presence of magnesium turnings (Mg) at about −75 to −65° C. to form a reaction product, followed by hydrolyzing the reaction product in effective contact with an aqueous hydrochloric acid solution at about 0 to 5° C.,
wherein $R_1$ and $R_2$ are identical or different and each represent a fluorine-substituted $C_1$–$C_9$ alkyl group, under conditions sufficient to produce a compound of the formula (2).

4. A method according to claim 1, further comprising reacting 1,2,4,5-tetramethylbenzene expressed by the following formula (3a) with iodine ($I_2$) and bromine ($Br_2$) in $CH_2Cl_2$ in the substantial absence of light and under other conditions sufficient to produce a compound of the Formula (3)

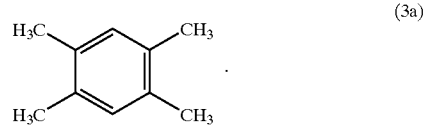

5. The compound as claimed in claim 1 wherein at least one of said R groups is trifluoromethyl.

6. The compound as claimed in claim 1 wherein all of said R groups are trifluoromethyl.

7. The method as claimed in claim 2 wherein at least one of said R groups is trifluoromethyl.

8. The method as claimed in claim 1 wherein all of said R groups are trifluoromethyl.

* * * * *